United States Patent [19]

Lundqvist et al.

[11] 4,318,180
[45] Mar. 2, 1982

[54] METHOD AND APPARATUS FOR INDICATING THE SIZE DISTRIBUTION OF PARTICLES IN A FLOWING MEDIUM

[75] Inventors: Inge J. Lundqvist, Spånga; Jan G. T. Pettersson; Gerdt H. Fladda, both of Täby, all of Sweden

[73] Assignee: Svenska Traforskningsinstitutet, Sweden

[21] Appl. No.: 47,002

[22] Filed: Jun. 11, 1979

[30] Foreign Application Priority Data

Jun. 15, 1978 [SE] Sweden ............................. 7806922

[51] Int. Cl.³ ..................... G06G 7/48; G01N 21/26
[52] U.S. Cl. ..................................... 364/555; 162/49; 162/263; 250/575; 356/442; 364/471
[58] Field of Search ............... 364/555, 471, 117, 573; 324/71 CP; 162/198, 263, 49; 356/442, 73; 250/573, 574, 575; 235/92 PC

[56] References Cited

U.S. PATENT DOCUMENTS

| | | | |
|---|---|---|---|
| 2,971,431 | 2/1961 | Glenn | 356/442 |
| 3,700,335 | 10/1972 | Seelbinder | 250/575 X |
| 3,807,864 | 4/1974 | Cornillaut et al. | 356/442 X |
| 3,822,095 | 7/1974 | Hirschfeld | 250/274 X |
| 3,916,197 | 10/1975 | Fulwyler | 250/575 X |
| 3,941,479 | 3/1976 | Whitehead | 364/555 X |
| 3,949,197 | 4/1976 | Bader | 324/71 CP X |
| 4,080,076 | 3/1978 | Carr | 356/442 |
| 4,110,044 | 8/1978 | Petterson et al. | 250/574 X |
| 4,146,799 | 3/1979 | Pitt et al. | 250/575 X |
| 4,171,916 | 10/1979 | Simms et al. | 162/263 X |

FOREIGN PATENT DOCUMENTS

| | | | |
|---|---|---|---|
| 2551231 | 5/1977 | Fed. Rep. of Germany | 364/555 |
| 1127342 | 9/1968 | United Kingdom | 364/555 |
| 1193840 | 6/1970 | United Kingdom | 364/555 |

Primary Examiner—Joseph F. Ruggiero
Attorney, Agent, or Firm—Lerner, David, Littenberg & Samuel

[57] ABSTRACT

Methods and apparatus for determining the particle size distribution with respect to selected fraction classes in the direction of flow of a medium are provided in accordance with the teachings of the present invention. A plurality of measuring configurations are employed to pass light through the medium to be measured and to detect the light transmitted therethrough. Each measuring configuration exhibits different resolution with respect to one another and particle size distribution for selected fraction classes is determined as a function of measuring signals derived by each of the plurality of measuring configurations from the transmitted light detected during a run of the medium and sensitivity coefficients of the measuring signals. The sensitivity coefficients employed are dependent upon the associated measuring configuration and fraction class. Thus rather than counting particles per se a measure of the concentration in each fraction class is obtained.

32 Claims, 6 Drawing Figures

SENSITIVITY OF THE AC-SIGNAL AS A FUNCTION OF THE MEAN FIBRE LENGTH OF THE FIBRE FRACTION FOR THREE DIFFERENT MEASURING DEVICE GEOMETRIES, RESOLUTIONS.

SENSITIVITY OF THE DC-SIGNAL AS AN INDIRECT FUNCTION OF THE MEAN FIBRE LENGTH OF THE FIBRE FRACTION FOR THREE DIFFERENT MEASURING DEVICE GEOMETRIES, RESOLUTION.

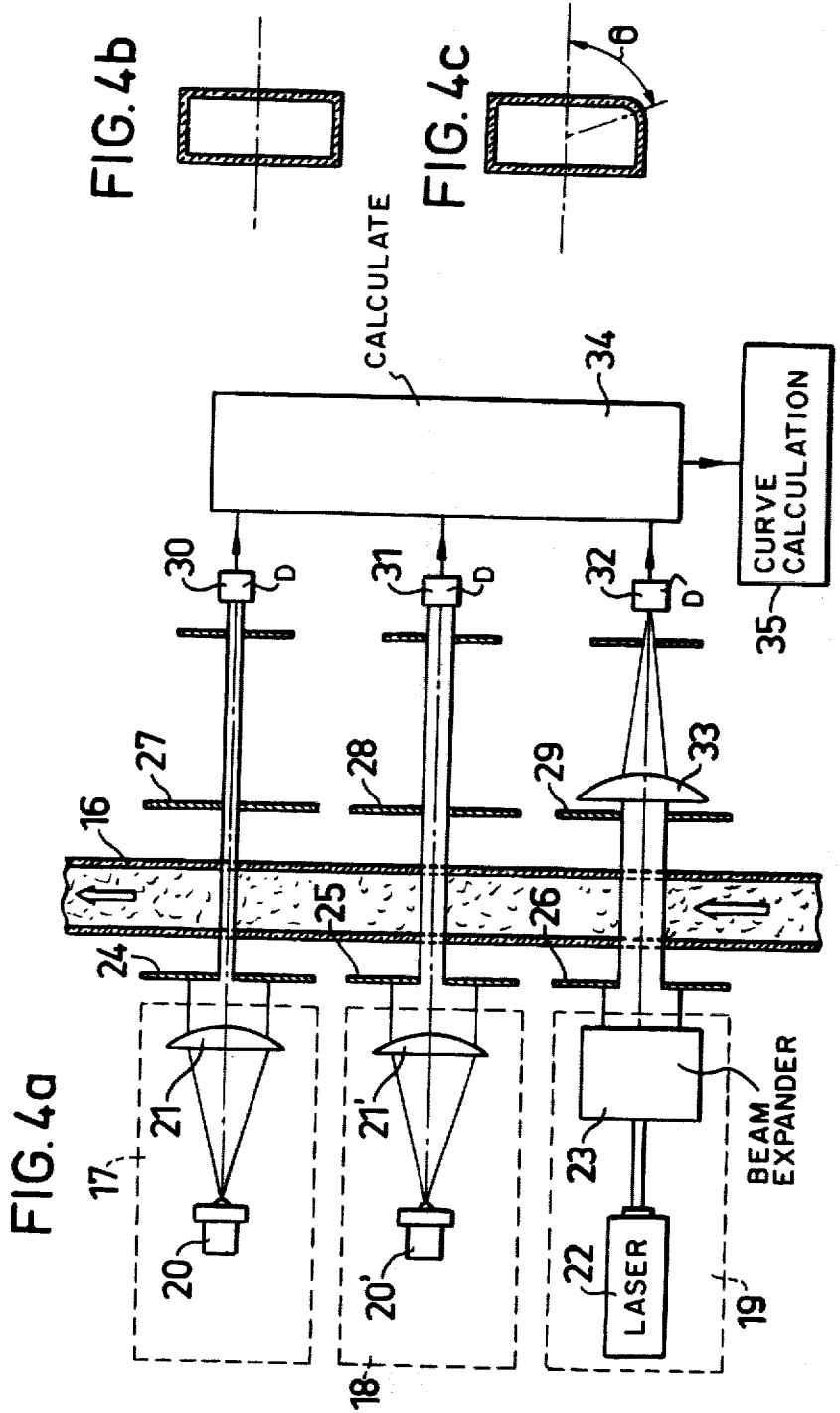

METHOD AND APPARATUS FOR INDICATING THE SIZE DISTRIBUTION OF PARTICLES IN A FLOWING MEDIUM

This invention relates to methods for determining particle size distribution, and to apparatus for carrying out such methods.

The invention can be utilized for indicating the distribution of the extension of particles in the flow direction in flowing media, which contain particles, for example fibres, when it is desired for some reason to know the distribution of the particles in different size fractions. A special application field for the method is the measuring of fibre suspensions, which are used as starting material for the manufacture of paper. The method, therefore, is described in the following with reference particularly to the measuring of paper pulp.

It applies to paper pulps of all types, for example mechanic pulps or chemical pulps, where the fractional composition of the pulp is of decisive importance for the properties of the paper to be manufactured. A higher proportion of long fibres, for example, results in an increase in strength. This rule, however, cannot be applied generally. For mechanical pulps, for example, not only is the content of long fibres of importance, but also the size distribution of the fibres in general. In order to obtain a pulp with paper-technical prerequisites, all fractions of the pulp must have good properties. In the case of mechanical pulps a varying proportion of fibre material in the so-called medium fraction of the pulp often has proved to give rise to varying properties of the resulting paper. It was, therefore, found desirable to develop a method, by which the content of at least three different fraction classes in the pulp, for example fine, medium and long fibre fraction, can be determined.

The same applies in a corresponding way to many chemical pulps, for example sulphite and sulphate pulp. Pulps of this kind should contain a high proportion of flexible long fibres and a fine material with binding tendency. This is obtained automatically, for example, for fully bleached unbeaten sulphate cellulose, as a consequence of the native properties of the wood, but the fraction composition of the fibrous suspension can be less favourable for chemical pulps of higher yield or for beaten low-yield pulps. Such pulps, therefore, require an increased control of the fraction composition, to render it possible to promptly detect deviations of the composition from the desired values so that the necessary corrective steps may rapidly be taken.

Heretofore, the proportions of different desired fractions were determined by taking a sample of the suspension.

The sample was then screened for the purposes of separating the different fractions from one another and thereafter the fractions dried and weighed. It is apparent that such a procedure is both expensive and especially slow; however, the same yields relatively accurate results. For some time now it has been desired to find a method for determining the proportions of desired fractions, which is safe and can be carried out quickly and preferably on a continuous basis. This desire now has been realized with the present invention. The method can be used both for providing a warning signal when the fractional proportions measured are not within predetermined limit values, and for effecting automatic adjustment of some element in the pulp manufacture, as for example adjustment of the beating discs during the manufacture of refined pulp.

The invention is based upon the basic signals utilized in the concentration determination method described in Swedish Pat. No. 7706320-4 corresponding to U.S. Pat. No. 4,110,044, where a method of obtaining a measure of the concentration of particles suspended in a liquid is disclosed. In this patent a method is described, according to which fraction distribution in a suspension is measured independent of concentration of fibre and also independent of light absorption in the liquid, in which the fibres are suspended. According to this patent the measuring result will only give information of the distribution of the amount (in MG/L) of long fibres in relation to the amount of short fibres in a suspension. This means that the method described in this patent is not intended to give a measure of the amount of fibres for a predetermined fraction. The measure is independent of the particle size distribution in the suspension and a signal is produced which varies linearly with the concentration. According to the teachings of this patent application, a signal is linearized which contains the square of the true effective value of the alternating voltage portion of a signal from a detector, which detects light having been projected through a suspension. Further a direct voltage signal is linearized which is obtained by a combination of the direct voltage portion of signals from a detector preferably located in 0°, or from two detectors located in different angular positions relative to the path of the light in the suspension. The linearization takes place with respect to the concentration. Variations in the sensitivity of the two signals, which hereinafter are called alternating voltage signal and, respectively, direct voltage signal are counterdirected with respect to the mean fibre length. In order to obtain a measure of the concentration independent of the fractional composition, in the Swedish Pat. No. 7706320-4, as mentioned, the alternating voltage signal and the direct voltage signal are linearized individually and given such inclinations, that the linearized signals when being added together have an equal sensitivity coefficient, i.e. the concentration measure is independent of the particle size distribution in the suspension.

As investigations of the two signals continued it was found, that the outgoing signals from the measuring unit comprising the detectors varied with the measuring geometry. The term measuring geometry here is understood to refer both to the location of the components and to their size and design, i.e. for example the surface of the detectors, the focal length of the lens system present in the measuring unit, the area of diaphragm utilized, the cross-section of the light beam and the physical dimensions in general. It was thereby found, that it is particularly the shape of the alternating voltage signal which is influenced by the measuring geometry, while the direct voltage signal substantially is influenced only by the geometry through a multiplicative constant, which is independent of the mean fibre length of the fibre material.

These physical conditions are utilized according to the present invention, which is described in greater detail in the following, with reference to the accompanying drawings, in which:

FIGS. 4a–4c show a second embodiment of apparatus for carrying out the method according to the invention wherein FIG. 4a illustrates such second embodiment per se and FIGS. 4b and 4c show the cross-sections of exemplary measuring bulbs used therein.

Figure 1:
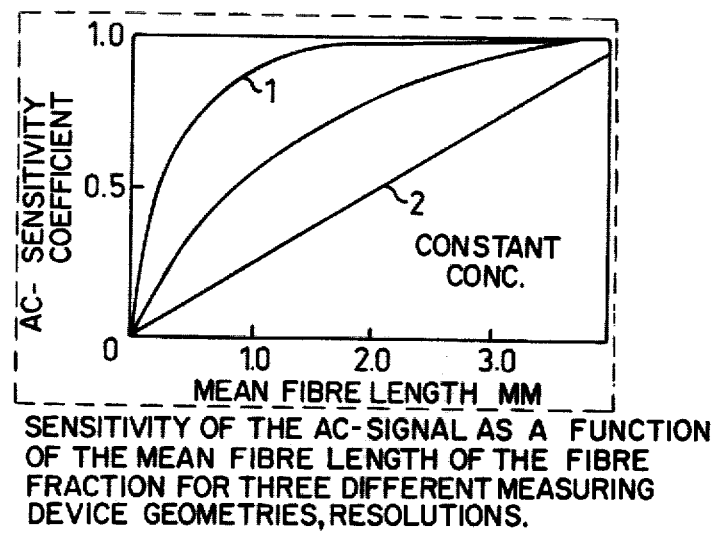
FIG. 1 is a diagram of different alternating voltage signals.

In FIG. 1 the sensitivity of the alternating voltage signal is shown as a function of the mean fibre length of the fibre fraction for three different measuring geometries, where of course the concentration of the suspension was maintained constant.

Figure 2:
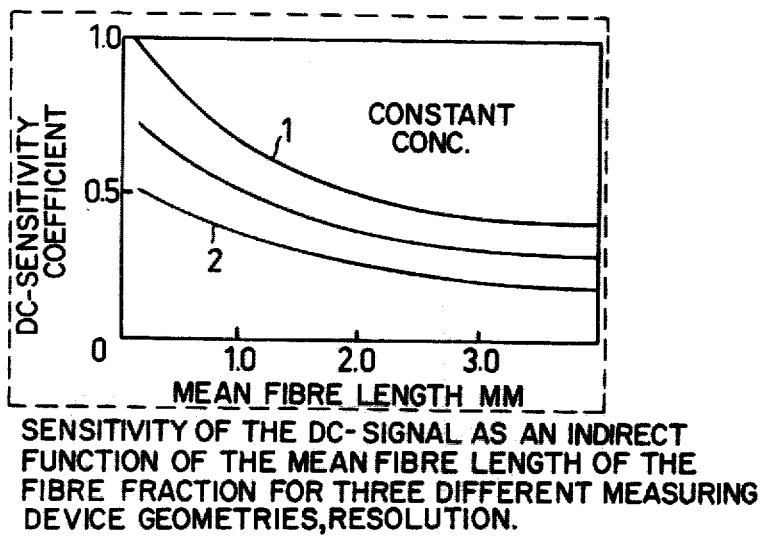
FIG. 2 is a diagram of different direct voltage signals.

In FIG. 2 the sensitivity of the direct voltage signal is shown as a function of the mean fibre length of the fibre fraction for three different measuring geometries, also at constant concentration. The curves designated by 1 are recorded with high resolution, i.e. small diaphragm dimension, small detector surface or the like, and the curves designated by 2 are recorded with low resolution. When the flow through the measuring bulb is accelerated, the fraction-selective procedure is more distinct at curve 1 in FIG. 1, due to the fact that the long fibres are aligned in the flow direction. It is, therefore, suitable to use a bulb with a cross-sectional area, which is smaller than that of the passageway used for flow through by the suspension, in order to obtain an accelerated flow through the bulb. The circumstance that it is just the alternating voltage signal, which changes in the way shown in FIG. 1, will be understood when it is realized, that at a finer resolution the detector senses a portion with a smaller cross-section of lighted material in the liquid. Conclusively, for covering the entire detection area in the longitudinal direction fibres with a shorter length are required than at a lower resolution, i.e. when the detector detects a greater cross-section of lighted material in the liquid. Therefore, the curve for high resolution proceeds faster to a constant value with increasing fibre length than the the curve for low resolution. The alternating voltage portion of the signal from the detector does not provide extra information on fibres exceeding a certain length. The alternating voltage signal, thus, is directly associated with the fibre length.

When a system is to be obtained, which shall render the equivalent content in a number of fraction classes desired to be measured, the dependence of the alternating voltage signal on the measuring geometry can be utilized. By disposing the matrices below and solving the equation system represented by them, the elements in K will represent the equivalent content of fibres expressed preferably in mg/l of the predetermined length fraction classes, i.e.

$$A K = U \tag{1}$$

where the elements in the matrix A are the sensitivity coefficients $a_{ij}$ for the different measuring geometries (rows) and length fractions (columns), and where i stands for geometry and j stands for length fraction. The elements in a row in the matrix A possibly may consist of the sensitivity coefficients of the DC-signals. The elements in the matrix K are the concentrations to be found of the different length fraction classes. The matrix K is a column vector. The elements in the matrix U are the linearized alternating voltage values from each of the measuring geometries at measurements of the suspension, the content of which is to be divided into classes. The matrix U is a column vector.

The input data obtained practically from the measurements, of course, will be impaired by certain measuring errors. It is, therefore, very important to use equations, which linearly are as independent as possible. In practice, therefore, it is not suitable to directly solve a system with measuring errors according to equation (1), but this equation is shown only for illustrating the principle. The equation system in practice should be built up, for example, according to the method of least squares. When the matrix A is chosen non-square (redundancy system), the method of least squares can be applied advantageously. The equation (1), therefore, according to known mathematic methods should be converted to:

$$(A^T A)^{-1} A^T U = K \tag{2}$$

Now the sensitivity coefficients $a_{ij}$ are to be found. An accurate method in this respect is to pass fractions, which are representative of each class and have known concentrations, through all measuring configurations, and to repeat this until fractions representative of all classes have been passed through. If, namely, a sample with mixed fraction content is passed through one of the measuring configurations, the i:th one, the following equation for the signal obtained can be drafted:

$$U_i = conc_1 a_{i1} + conc_2 a_{i2} + \ldots + conc_n a_{in}$$

where $conc_1$ is the concentration fibre content in the first class, and $conc_n$ is the concentration fibre content in the last class. The different coefficients $a_{ij}$, thus, are obtained by the above run with fractions with separate known class and known concentration. It is, thus, apparent from the aforesaid that the entire fraction content is divided into the number of fraction classes, which are desired to be measured. The selected classes are adjoining each other, and the fibre fraction content is covered to 100 percent.

This shows, that for obtaining an equation system providing full coverage for the entire range with n fraction classes n−1 conditions are required. This should indicate that it also is necessary to use a number of measuring configurations of n−1.

It is possible, however, to manage with one less measuring configuration, because the direct current signal from one of the measuring configurations in fact yields one extra condition and can be used like an alternating voltage signal received from a measuring configuration. The number of measuring configurations used, therefore, can be reduced to n−2, even when at experiments with the method preferably as many measuring configurations are used as there are selected classes. It should be observed, that the term different measuring configurations is to be understood as different measuring head units with different measuring geometry, which implies that not all elements in the different configurations must be different. It may be sufficient, if one element, for example a diaphragm or a detector, is varied. Multiple detectors, for example, can be used whereby one condition can be obtained from the signal from a partial detector, and a second condition can be obtained from the signal from the entire multiple detector. The essential feature is, as mentioned above, that the different measuring configurations yield different resolution relative to each other.

There exist, of course, also other methods than the one described above for obtaining the coefficients in the matrix A. It is possible, for example, to run several different samples with known fraction content distributed over different classes, and in this way, though more troublesome, to obtain the different coefficients in the matrix A.

It is not necessary, of course, when building-up measuring apparatus to carry out the relatively troublesome measuring of all coefficients in the matrix A individually for each apparatus. This would render such apparatus much more expensive. It can be sufficient to use coefficients obtained by measurements of a prototype. In order to ensure that the separate apparatus yield measuring results lying within permissible limits, one or several media with a suitable fraction content can be run as reference through the apparatus and be measured. Apparatus not fulfilling the requirements are adjusted by adjusting especially the mechanical and optical parts of the different measuring configurations. The coefficients in the matrix A preferably are stored in a fixed memory, for example of the type ROM, PROM or EPROM, in the calculation part of the apparatus. At the manufacture it is in most cases cheapest to make these memories identical.

In many cases it is not necessary, either, to calibrate the apparatus so as to yield accurately correct values of the fraction content in every class, and approximative values may be sufficient, because the apparatus often are to be used to indicate changes in the fractionary composition of a medium between different measurements. The apparatus in this case can be said to be self-defining. Thus, as it is a question of comparative measuring, the different coefficients can be chosen relatively arbitrarily.

It is also obvious that the value, which the apparatus indicates for every fraction class at a measuring, does not need to be the value of the accurate fraction amount within these classes nor the accurate value of the percentage of fraction within the classes in question. It can, instead, be very useful to see to it that the values indicate a definite figure, for example 0, when the values for the classes are in agreement with a desired value. The apparatus thereby indicates deviations from a desired composition. The system can be made still more sophisticated by varying the scales for the different classes in relation to their importance for the final result.

It is also possible by the method according to the invention to obtain a percentage-indicating system, by utilizing the quotas between the alternating voltage signals and the direct voltage signals from the respective measuring geometries. The value of these quotas varies in precisely the same manner as in the afore-described concentration-indicating measuring system with length fraction and measuring geometry, but in addition it is independent of concentration. By using here the concentration-independent quotas as the sensitivity coefficients, the elements $a_{ij}$ in the matrix A, a similar equation system can be drawn up which directly yields the equivalent content by percentage in the preselected length fraction classes. The matrix U in this case are the quota signals received for the respective measuring geometry at the measuring of the fibre suspension in question. In practice, of course, the percentages added together will not be accurately 100 percent, unless special measures are taken. The fibre length distribution curve has a continuous course and can only be approximated by indicating the content in a finite number of classes. It is also possible, instead of using pure quota formation between the alternating voltage signal and the direct voltage signal, to use the more complex quota formation as described in the Swedish Pat. No. 77063204-4, viz.

$$T_F = \frac{\alpha V_{AC} + \beta V_{DC}}{V_{AC} + V_{DC}} = \frac{\alpha \mu + \beta \nu}{\gamma \nu \gamma \nu}$$

where $V_{AC}$ and $V_{DC}$ are the alternating voltage signal and, respectively, the direct voltage signal, $\mu$ is a factor, which is constant for a given fraction distribution for the measuring head in question and, thus, varies only in dependence on the fraction distribution, $\nu$ is a factor, which is constant for a given fibre fraction for the measuring head in question and, thus, varies only in dependence of the fraction distribution, and $\alpha$, $\beta$, $\gamma$, $\delta$ are constants.

The more complex signal received hereby from every measuring head is very useful, because in addition to its use by the aforementioned equation system for directly determining the proportion of fibre material in selected fraction classes, said signal also can be used for indicating fraction distribution tendencies within every individual class.

It is known by experience that the curve for the concentration as a function of the fraction distribution in most cases is a continuous distribution function with a positively oblique distribution, similar to an F-distribution curve. The factor of particular interest at the measuring of paper pulp are the changes in the shape of this curve, i.e. whether and if, in which degree the top of the curve is displaced between fraction classes, and whether the curve for some reason should change character in general.

Therefore, the values obtained according to the aforementioned equation system $K=A^1U$ or $K=A^TU$ $(A^TA)^{-1}$ can be used so, that the values, or some suitable fraction thereof, are marked somewhere within their respective size distribution intervals, where they with greatest probability are to be located independently of whether only the alternating voltage values, the alternating voltage values simply divided by their respective direct voltage values, or the formula $T_F$ are used. By marking in these places the height of the marked values, an approximate knowledge of the course of the curve can be obtained, and very definitely a knowledge of the tendencies of changes in one direction or the other is obtained. When the aforesaid equation for $T_F$ is used, a still better approximate knowledge of the curve course can be obtained, because in addition to to the size of the signals, each indicating the proportion of fibre material within a definite fraction, also an indication is obtained where within the respective interval the value is to be marked. As is apparent from the Swedish patent No. 7706320-4, the formula $T_F$ yields an indication of the fraction distribution with respect to long fibres in relation to short ones. In this case it is suitable to directly feed the different calculated values for $T_F$ obtained from the different measuring heads into a special computer unit, which by knowledge of the distribution function directly delivers at its output the calculated curve formula and possibly also the tendency thereof in relation to the curve shapes previously obtained. A further variant of application for calculating the fraction proportion within each interval is obtained when both the alternating voltage signals or, alternatively, the alternating voltage signals simply divided by the direct voltage signals are used and simultaneously the $T_F$-signals are calculated. By inserting the alternating voltage signals, or the alternating voltage signals simply divided, in the above equation system $KA = U$, the proportion of fibre material within the selected fraction classes is calculated, and by inserting calculated $T_F$-values in a similar equation system, the positions along the fraction axis within each interval are obtained, at which positions the different measuring values most suitable are to be marked.

Figure 3:
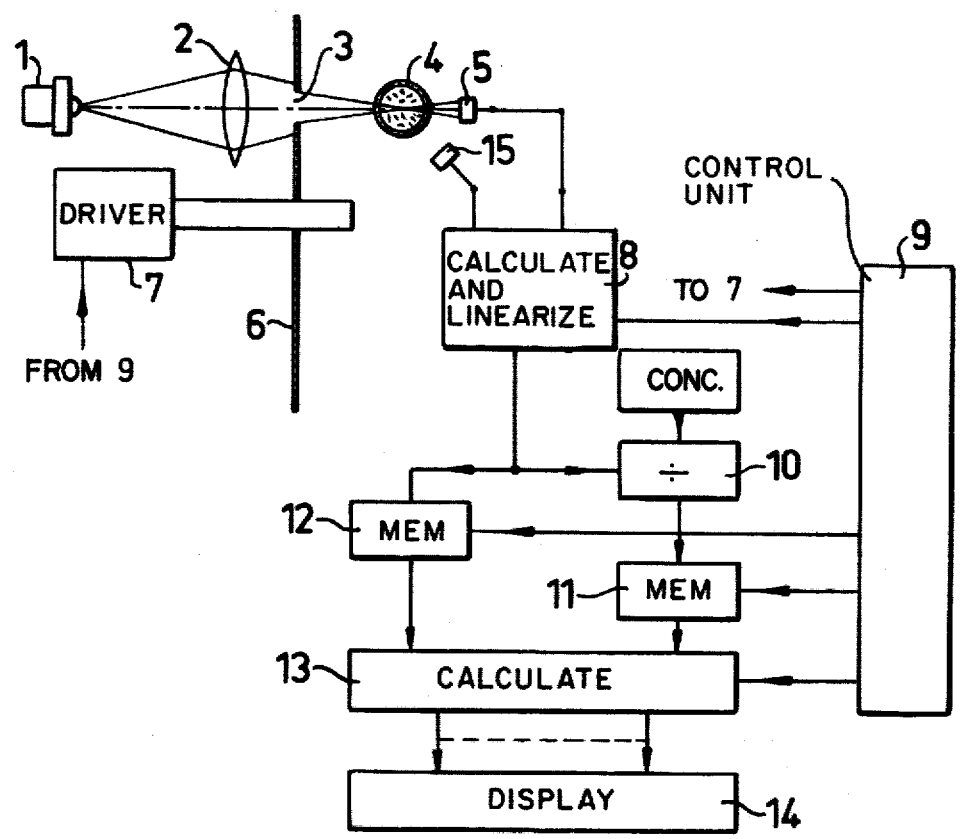
FIG. 3 shows a first embodiment of apparatus for carrying out the method according to the invention.

In FIG. 3 a first embodiment of an apparatus for carrying out the method according to the invention is shown. The radiation from a light source 1 is focused via a lens system 2 and a diaphragm 3 to the centre of a bulb 4 with circular cross-section containing a flowing medium. On the bulb side opposed to the light source a detector 5 is located.

The output of the detector 5 is coupled to a calculation and linearization circuit 8, which carries out the calculation $$\ln\left[\frac{V_{RMS}^2}{c_2} \frac{V_{DC(0°)}^2}{V_{DC(0°)}^2} + 1\right]$$

which is the aforementioned linearized alternating voltage component, and where $V^2_{RMS}$ is the square of the true effective value of the alternating voltage signal from the light detector 5, $V_{DC(0°)}$ is the direct voltage portion of the signal from the detector 5 at the measuring of medium without suspended substances, and $c_2$ is a constant. An example of a circuit carrying out this calculation is disclosed in said Swedish patent 7706320-4.

In the Figure further is shown that the diaphragm 3 is mounted on a rotary disc 6, which is provided with several diaphragms distributed over a ring on the disc. When the number of desired measurable fraction classes is n, the number of diaphragms j can vary from $n-2$ to any number. This is due to the fact, as already mentioned, that the direct voltage signal from one of the measuring configurations per se can be used as if it were an alternative voltage signal, because it yields an extra condition for determining the fraction composition. Thereby one row in the matrix A is obtained. A further measuring configuration is not necessary, because the entire fibre length range is covered. All this together implies that it is possible to manage with $n-2$ measuring configurations. The disc is operated by a drive unit 7, which by control from a control unit 9 rotates the disc 6 so that a new diaphragm is introduced into the beam path from the lamp 1. The control unit 9 also controls the circuit 8. Instead of the rotary disc with diaphragms 3 of fixed setting, an iris diaphragm, for example, can be used which can be set in different positions. For obtaining the coefficients in the matrix A in a suitable way, first a suspension of known concentration with fibre class 1 which, for example, may be 200 mesh from a Bauer-McNett fractionation, is passed through the bulb 4, and the linearized alternating voltage value for each of the diaphragms 3 is indicated. These values are divided by the concentration in a divider 10 and stored in a memory 11 by control from the control unit 9, which thereby addresses the memory in a suitable way. The remaining suspensions with fractions within the desired fraction classes then are passed in due succession through the bulb, and the output signals from the circuit 8 for each diaphragm 3 divided by the known concentrations are stored in the memory 11 in the same way as for the fraction in the class 1. When, for example, three fraction classes for paper pulp are to be chosen, the fine fraction, for example, is chosen 200 mesh, the medium fraction is chosen 200–30 mesh, and the long fibre fraction is chosen 30 mesh. It is to be observed, that the suspensions used with known fraction content really must be representative of their class and, thus, contain a fraction composition, which is uniformly distributed over the class. At this method, thus, the values are stored in the aforesaid matrix A in the memory 11. Of course, this need not occur as often as the measurings proper, but only upon a special essential demand. The memory 11, therefore, can be a non-programmable fixed memory. It need not be designed separately for each measuring apparatus, but only as a prototype. Calibration of the apparatus, if necessary, can be carried out by adjusting the optical units.

At the measuring proper for each diaphragm 3 the output signals from the circuit 8 are stored by control from the control unit 9 in a second memory 12, which can be of a temporary type. When the memory 12 is filled, the calculating unit 13 carries out the calculation of the desired concentrations, also by control from the control unit 9. The calculating unit preferably consists of a pre-programmed micro- or mini-computer, which carries out the calculation of the aforesaid equation systems and presents the results on a display unit 14, or delivers an analog or digital control signal, which is in definite relation to the results obtained. When a percentage-indicating system is desired, the alternating voltage signal obtained is divided in this present case by $$\frac{\ln V'_{DC(0°)}}{V_{DC(0°)}}$$

In FIG. 3 also a second detector 15 is shown, which is located in an angular position relative to the optical axis, which position is different from that of the detector 5. Said detector 15 is used in cases when a system is desired which depends on intensity and colour, and it provides at quota formation of the alternating voltage signal by guidance of the direct voltage portions from the two detectors also a percentage-indicating system. By help of the direct voltage portion of the signal from the detector 15, the calculation circuit carries out the aforesaid direct voltage signal according to the formula $$\ln\left[\frac{\frac{V_{DC(\theta°)}}{V_{DC(0°)}} = \frac{V_{DC(\theta°)}}{V_{DC(0°)}}}{c_1} + 1\right]$$

where $V_{DC(\theta°)}$ is the direct voltage signal obtained at the measuring of the suspension from the detector 15 located in the angular position $\theta°$, $V_{DC(0°)}$ is the direct voltage signal obtained at the measuring of the suspension from the detector 5 in the angular position 0°, $V'_{DC(\theta°)}$ and $V'_{DC(0°)}$ are the direct voltage signals from the detectors 15 and 5 at the measuring of a medium without particle suspension, and $c_1$ is a constant.

An example of how the calculating unit may be designed for carrying out this operation is shown in the Swedish Pat. No. 7706320-4. As mentioned above, a quota formation between the alternating voltage signals and the direct voltage signals is carried out in the percentage-indicating systems, which quota formation also is carried out in the circuit 8. In other respects the circuits in FIG. 3 operate in precisely the same way for the percentage-indicating systems as for the concentration-indicating one.

In FIG. 4a a second embodiment of an apparatus for carrying out the method according to the invention is shown, in which the suspension is passed through a substantially square bulb 16, which in FIG. 4a is shown by way of a longitudinal section. FIG. 4b is a cross-section of the bulb when the apparatus is to be used in a concentration-indicating system, and FIG. 4c is a cross-section of a bulb adapted for use in a percentage-indicating system where the second detector corresponding to the detector 15 in FIG. 3 is located in the angular position $\theta°$. The corner of the bulb here is rounded so that the light meeting the detector 15 from the suspension is to meet the glass wall of the bulb perpendicularly. This design is suitable for use in this case, but not entirely necessary, because also a compensation for curved beam path can be made.

As appears from FIG. 4a, the bulb 16 in this case is lighted by three beam sources 17,18,19 with collimated light. These beam sources preferably are of the same type relative to one another, though two types of beam sources are shown in the Figure in order to indicate, that both these types can be applied. The beam sources 17 and 18 here are shown to comprise a lamp 20,20' and a lens system 21,21', which collimates the light from the lamp, and the beam source 19 is shown to comprise a laser 22 with a subsequent so-called beam expander 23.

In the beam direction before the bulb, a diaphragm 24,25 and, respectively, 26 is located to limit the beam path from each of the beam sources. In the beam direction after the bulb, additional beam path diaphragms 27, 28 and, respectively, 29 are located. These latter ones determine the optical angle for the detectors 30,31 and 32, one for every beam path. In the Figure is shown that the diaphragms 24-26 in the beam path before the bulb and the diaphragms 27-29 after the bulb have the same aperture for the same beam path. This is not entirely necessary.

In the Figure the uppermost measuring device configuration 17,24,27,30 has the highest resolution, i.e. the diaphragms 24 and 27 have here their smallest area, and the lowermost measuring device configuration 19,26,29,32 has the lowest resolution, i.e. the diaphragms 26 and 29 have here their largest area, which here is so large that a collecting lens 33 had to be installed after the diaphragm 29 for collecting the radiation on the detector 32. A greater detecting surface, of course, could have been used, instead.

The signals from the detectors 30-32 are fed in parallel to a circuit 34, which may have substantially the same design as the circuit in FIG. 3, or as the calculating circuits according to the Swedish Pat. No. 7706320-4, or as both these types of circuits for co-operation, with the exception that the detector signals first are stored so that they can be processed subsequently in series by the calculating circuit 8. The output from the circuit 34 here is coupled to a circuit 35, which effects a calculation of the curve shape for the distribution function for the fraction distribution. Both the circuit 34 and the circuit 35, of course, may be parts of the same unit, for example a minicomputer, which at its output delivers a suitable control signal in response to the appearance of the calculated main shape.

The invention, of course, is not restricted to the embodiments described above. Many of the moments, for example, which in the circuit according to FIG. 3 are shown carried out automatically by control from a control unit 9 can be carried out manually with manual reading and calculation of the results obtained. This applies especially to the calibration part. It is even imaginable, if the details comprised, such as lighting, diaphragm arrangement, detectors and the mechanical coupling between the details and the bulb used are sufficiently stable, that the memory 11 is a fixed memory, which is programmed at the manufacture of an apparatus whereafter no adjusting re-programming is required.

The method according to the invention is of excellent use when rapid observation of tendencies in a change having occurred is desired. It can be very important to know, which fibre length range has the highest value and if this special fibre length range shifts toward fine fraction or long fibre fraction. Such tendencies of changes and fluctuations thereof can provide valuable information on which part of the paper pulp manufacturing process requires corrective measures.

The method has yielded excellent results at test runs. At a comparison with simultaneous measuring by the previously normal method described above in the introductory portion it was found, that the values obtained lie entirely within expected margins of error, which are due to the fact that no method of this kind can yield an entirely absolute result, because it is extremely difficult to obtain a boundary between two adjacent fibre length ranges which is fully sharp, but a certain overlapping must occur irrespective of the method being used.

We claim:

1. A method of determining particle size distribution with respect to fraction classes in the direction of flow in a flowing medium containing particles comprising the steps of:

establishing a plurality of measuring configurations for illuminating portions of said medium containing a plurality of particles and detecting light transmitted through said portions of said medium containing said plurality of particles, each of said plurality of measuring configurations exhibiting a different resolution for illuminating portions of said medium and detecting light transmitted therethrough representing differing cross-sectional portions of said medium, each differing cross-sectional portion of said medium containing a plurality of particles;

illuminating a portion of said medium containing a plurality of particles through one of said plurality of measuring configurations and detecting light transmitted through said portion of said medium containing said plurality of particles;

converting light detected from said one of said plurality of measuring configurations into a first measuring signal representative of the plurality of particles within said cross-sectional portion represented by said one of said plurality of measuring configurations;

illuminating a portion of said medium containing a plurality of particles through another of said plurality of measuring configurations and detecting light transmitted through said portion of said medium containing said plurality of particles;

converting light detected from said another of said plurality of measuring configurations into a second measuring signal representative of said plurality of particles within said cross-sectional portion represented by said another of said plurality of measuring configurations; and determining the particle size distribution by employing first and second measuring signals from said measuring configurations obtained during a run of said medium and sensitivity coefficients of said measuring signals, each of said coefficients being dependent upon a measuring configuration of a fraction class.

2. The method defined in claim 1, further comprising the step of determining the sensitivity coefficients of the measuring signals for the selected fractions and the measuring configurations by passing and measuring a number of said fractions each of which is representative of one of the fraction classes into which the fraction range is divided through all measuring configurations.

3. The method defined in claim 1, further comprising the steps of determining the sensitivity coefficients of the measuring signals for selected fractions and the measuring configurations by passing and measuring a number of samples with known fraction composition through all measuring configurations.

4. The method defined in claim 1, further comprising the step of choosing an indication of the measuring signals by allotting during a measuring of a medium with a standardized desired composition the values obtained for the different fraction classes with predetermined values.

5. The method defined in any of claims 2, 3, 4, or 1, further comprising the steps of forming and squaring an effective value of an alternating current voltage portion of the measuring signals received from each of the measuring configurations.

6. The method defined in claims 2 or 3, further comprising the steps of forming and squaring at the obtaining of the sensitivity coefficients of the measuring signals the effective value of an alternating current voltage portion of the signal received from each of the measuring configurations, and forming the direct current voltage portion from each of the measuring configurations obtained at the running of samples representative for one of the fraction classes, each of these values obtained comprising the basis for calculating one of the sensitivity coefficients.

7. The method defined in claim 1, further comprising the step of linearizing the measuring signals with respect to concentration, whereby the equations used for deducing the weight proportion of particles in every class becomes linear.

8. The method defined in claim 7, wherein said linearization step comprises forming a linearized effective value signal according to the formula $$\ln\left[\frac{V^2_{RMS}}{c^2} \frac{V^2_{DC(0°)}}{V'^2_{DC(0°)}} + 1\right]$$

where $V^2_{RMS}$ is the square of the effective value of an alternating current voltage signal from a first light detector, $V_{DC(0°)}$ and $V'_{DC(0°)}$ are the direct current voltage portion of the signal from the first detector obtained during a measuring of a medium with suspended substances and during a measuring of a medium without suspended substances respectively, and $c_2$ is a constant.

9. The method defined in claim 8, further comprising the step of obtaining values of the weight proportion of particles in the selected fraction classes expressed in percent of the total particle concentration in the medium for each measuring configuration by dividing the alternating current voltage signal by $\ln V'_{DC(0°)}/V_{DC(0°)}$.

10. The method defined in claim 8, further comprising the steps of obtaining values of the weight proportion of particles in the selected fraction classes expressed in percent of the total particle concentration in the medium for each measuring configuration by indicating light emitted from the medium in a definite direction different from the optical axis using a second light detector, forming a linearized direct voltage signal according to the formula $$\ln\left[\frac{\frac{V_{DC(\theta°)}}{V_{DC(0°)}} \frac{V_{DC(\theta°)}}{V_{DC(0°)}}}{c_1} + 1\right]$$

where $V_{DC(0°)}$ is the direct current voltage portion obtained during a measuring of a medium with suspended substances at the angle 0°, $V'_{DC(0°)}$ is the direct current voltage portion during a measuring of a medium without suspended substances of the signal from the first light detector, $V_{DC(\theta°)}$ is the direct current voltage portion at the measuring of a medium with suspended substances at the angle $\theta°$, $V'_{DC(\theta°)}$ is the direct current voltage portion obtained during a measuring of a medium without suspended substances of the signal from a second light detector, and $c_1$ is a constant and forming for each measuring configuration the quota between the linearized alternating voltage signal and the linearized direct voltage signal.

11. The method defined in claim 7, further comprising the step of forming for each measuring configuration a signal according to the formula $$T_F = \frac{\gamma V_{AC} + \beta V_{DC}}{\gamma V_{AC} + \sigma V_{DC}}$$

where $V_{AC}$ is a linearized alternating current voltage signal, $V_{DC}$ is a linearized direct current voltage signal, and $\alpha$ $\beta$ $\delta$ $\rho$ are constants, the values obtained for said signals comprising the starting values from which the weight proportion of particles in every selected class is indicated.

12. The method defined in claim 1, wherein said determining step comprises using an equation system for calculating the weight proportion of particles in the given fraction classes of the type $K=A^{-1}$ or $K=(A^TA)^{-1}A^TU$, where A is a matrix, in which the elements of said matrix A are the sensitivity coefficients of an alternating current voltage and direct current voltage signal for the different measuring geometries represented as rows of said matrix A and length fractions represented as columns of said matrix A measured on the fractions, which are representative of the fraction classes required, $A^{-1}$ is the inverted matrix A, $A^T$ is the transposed matrix A, U is a column matrix where the elements are linearized alternating current voltage values from each of the measuring geometries during measurings of the suspension, the content of which is to be divided into classes, and where U is a column matrix where the elements are the wanted concentrations or the wanted percentages for the different length fraction classes.

13. The method defined in claim 1 further comprising the steps of making calculated values of weight proportion of particles in the selected fraction classes in a coordinate system with the fraction along the abscissa and the particle along the ordinate in such manner that predetermined fractions of the calculated values for each fraction class are marked in a predetermined place along the abscissa within each fraction class, and calculating, using knowledge of the general appearance of the fraction distribution plot in a coordinate system, a curve for the medium with the unknown fraction composition.

14. The method defined in claim 11, wherein said determining step comprises individually calculating the alternating current voltage values or the alternating current voltage values divided by respective direct current voltage values, deriving the values of the fractions within the respective classes by using said values calculated in said previous step, forming the signal $T_F$ for every measuring configuration by using a suitable choice of constants $\alpha$, $\beta$, $\delta$, $\rho$, marking an indication along an abscissa within the respective classes a predetermined fraction of the values for the fractions for each class along the ordinate in a coordinate system with the fraction along the abscissa and the particle amount along the ordinate, and calculating, by using knowledge of the general appearance of the fraction distribution plot in a coordinate system, a curve for the medium with the unknown fraction.

15. Apparatus for indicating particle size distribution with respect to fraction classes in a flowing medium containing said particles, said apparatus comprising:
  measuring configuration means for illuminating a plurality of portions of said medium and for detecting light transmitted through each of said plurality of portions of said medium to provide a plurality of measuring signals, each of said plurality of portions of said medium illuminated containing a plurality of particles and being illuminated and having light detected therefrom by said measuring configuration means to cause light detected from each of said plurality of portions to exhibit differing light resolutions corresponding to a different cross-sectional area for each portion and differing fields of vision and different sensitivity coefficients relative to one another; and
  means responsive to said plurality of measuring signals obtained during a passage of said medium through said measuring configuration means and said sensitivity coefficients for determining the particle size distribution of said medium with an unknown particle composition for each of said fraction classes, each of said sensitivity coefficients being dependent upon the manner in which each of said plurality of portions of said medium is illuminated by said measuring configuration means and the fraction classes associated therewith.

16. The apparatus defined in claim 15, wherein said measuring configuration means comprises a measuring unit including a light source element, an optical element, a diaphram element and a detector element, at least one of said elements being adjustable or exchangeable to provide said differing resolutions.

17. The apparatus defined in claim 15, wherein said measuring configuration means comprises individual measuring units located in a side by side relationship, each of said plurality of measuring configuration means including a light source, a detector and optics located between said source and said detector.

18. The apparatus defined in any one of claims 16, 17, or 15, further comprising a cylindric bulb for conveying said medium, said bulb having an axis of symmetry and walls transparent to light emitted by said measuring configuration means, said measuring configuration means including a light source and means to focus the light from at least said light source on the axis of symmetry of the bulb.

19. The apparatus defined in any one of claims 16, 17, or 15, further comprising a bulb for conveying said medium, said bulb having plane sidewalls perpendicular to the direction of light emitted by said measuring configuration means, said light means including optical means for illuminating the bulb with collimated radiation.

20. The apparatus defined in claim 15, wherein said for determining means comprises a calculation and linearization circuit responsive to detected light transmitted through said medium.

21. The apparatus defined in claim 15, wherein said means for determining comprises first memory means for storing sensitivity coefficients of the measuring signals, second memory means for temporarily storing values representative of the measuring signals obtained during a passing of a medium having unknown fraction composition through all said measuring configuration means, and calculation unit means responsive to contents in said first and second memory means for calculating a required indication of the fraction composition.

22. The apparatus defined in claim 21, wherein said first memory means comprises a fixed memory.

23. The apparatus defined in any one of claims 16 or 17, further comprising means for filtering out a direct current voltage portion of a signal resulting from detecting the light transmitted through said medium.

24. The apparatus defined in claim 20, wherein said measuring configuration means comprises a detector means for detecting light transmitted through said medium, said detector means and said calculation and linearization circuit having a DC filter coupled therebetween, the calculation and linearization circuit carrying out a calculation according to the formula $$\ln\left[\frac{V^2_{RMS}}{C_2} \times \frac{V^2_{DC(0°)}}{V'^2_{DC(0°)}} + 1\right]$$

where $V_{RMS}$ is the true effective value of the alternating current portion of the output signal from the detector means, $V_{DC(0°)}\gamma$ and $V'_{DC(0°)}\gamma$ are the direct voltage portion of the signal from the detector means during the measuring of a medium with suspended substances and at the measuring of a medium without suspended substances respectively, and $c_2$ is a constant, said calculation and linearization circuit including a memory means for storing values of $\gamma$ and $V'_{DC(0°)}$.

25. The apparatus defined in claim 24, wherein the linearization and calculation circuit additionally acts to carry out a division by $\ln V'_{DC(0°)}/V_{DC(0°)}$.

26. The apparatus defined in claim 24, further comprising an additional detector for indicating light scattered from the medium in a direction apart from an axis along which the transmission of light through the medium occurs, and circuit means for filtering a direct voltage portion of the signal from said additional detector, which portion is fed to said calculation and linearization circuit, said calculation and linearization circuit carrying out the calculation $$\ln\left[\frac{\frac{V_{DC(0°)}}{V'_{DC(0°)}} - \frac{V_{DC(\theta°)}}{V'_{DC(0°)}}}{c_1} + 1\right]$$

where $V_{DC(0°)}$ and $V'_{DC(0°)}$ are the direct voltage portions of the signal from the detector means during the measuring of a medium with suspended substances and a medium without suspended substances, respectively, $V_{DC(0°)}$ and $V'_{DC(0°)}$ are the direct voltage portion of the signal from the additional detector during the measuring of a medium with suspended substances and a medium without suspended substances, respectively, and $c_1$ is a constant, and said calculation and linearization circuit including a memory for the storage of values for $V_{DC(0°)}$ and $V'_{DC(0°)}$.

27. The apparatus defined in claim 26, wherein the calculation and linearization circuit additionally acts to carry out a division between the first and second formulas recited.

28. The apparatus defined in claim 24, wherein the linearization and calculation circuit carries out the calculation $$T_F = \frac{\alpha V_{AC} + \beta V_{DC}}{\gamma V_{AC} + \sigma V_{DC}}$$

where $V_{AC}$ is the linearized alternating voltage portion of said signal, $V_{DC}$ is the linearized direct voltage portion of said signal, and $\alpha$, $\beta$, $\gamma$, $\sigma$ are constants.

29. The apparatus defined in claim 21, wherein said calculation unit means uses the calculated values of the fraction content in different fraction classes and the general appearance of a distribution function stored in the calculation unit to calculate the fraction distribution curve for a medium with unknown fraction composition.

30. Apparatus for determining the particle size distribution with respect to fractional classes in a flowing medium containing said particles, said apparatus comprising means for illuminating portions of said medium containing a plurality of said particles, means for converting into a measuring signal light transmitted through said medium, said converting means including first and second light detectors disposed at different angles with respect to said means for illuminating portions of said medium containing a plurality of said particles and said medium, and means for imparting a plurality of resolutions to light transmitted through said medium and detected by at least one of said first and second light detectors, each of said plurality of resolutions corresponding to a different cross-sectional area for portions of said medium illuminated and each different cross-sectional area containing a portion of said medium containing a plurality of said particles.

31. The apparatus defined in claim 30, wherein said means for illuminating comprises a light source and said means for imparting takes the form of a rotating disc having a plurality of different size holes, whereby said plurality of resolutions are achieved.

32. The apparatus defined in claim 30, wherein said means for illuminating comprises a plurality of light sources and said means for imparting takes the form of diaphram means for each of said plurality of light sources, each of diaphram means having different beam widths, whereby said different resolutions are achieved.

* * * * *